United States Patent [19]

Sie

[11] Patent Number: 5,216,034

[45] Date of Patent: Jun. 1, 1993

[54] PROCESS FOR THE PRODUCTION OF METHANOL

[75] Inventor: Swan T. Sie, Amsterdam, Netherlands

[73] Assignee: Shell Oil Company, Houston, Tex.

[21] Appl. No.: 783,187

[22] Filed: Oct. 28, 1991

[30] Foreign Application Priority Data

Oct. 29, 1990 [GB] United Kingdom ................ 9023465

[51] Int. Cl.$^5$ ...................... C07C 27/06; C07C 27/08
[52] U.S. Cl. ................................................... 518/706
[58] Field of Search ........................................ 518/706

[56] References Cited

U.S. PATENT DOCUMENTS 3,598,527 8/1971 Quartulli et al. ..................... 518/706
4,235,799 11/1980 Wentworth et al. ................ 518/706

OTHER PUBLICATIONS

Westerterp et al, Ind. Eng. Chem. Res, 1989, 28, 763-771.
Post et al, Chemeca '88, Australias Bicentennial International Conference for the Process Industries, Sidney, Aug. 28-31, 1988.
Saito et al, AICHE Symposium No. 262, vol. 84, pp. 102-113, 1988.

Primary Examiner—Howard T. Mars
Attorney, Agent, or Firm—Y. Grace Tsang

[57] ABSTRACT

A process for the production of methanol by reacting a gaseous mixture comprising hydrogen and carbon monoxide in the presence of a catalyst composition in a fluidized bed while cooling, characterized in that the reaction is carried out in a plurality of fluidized catalyst bed reactors in series with interstage removal of methanol from the reaction mixture.

6 Claims, 1 Drawing Sheet

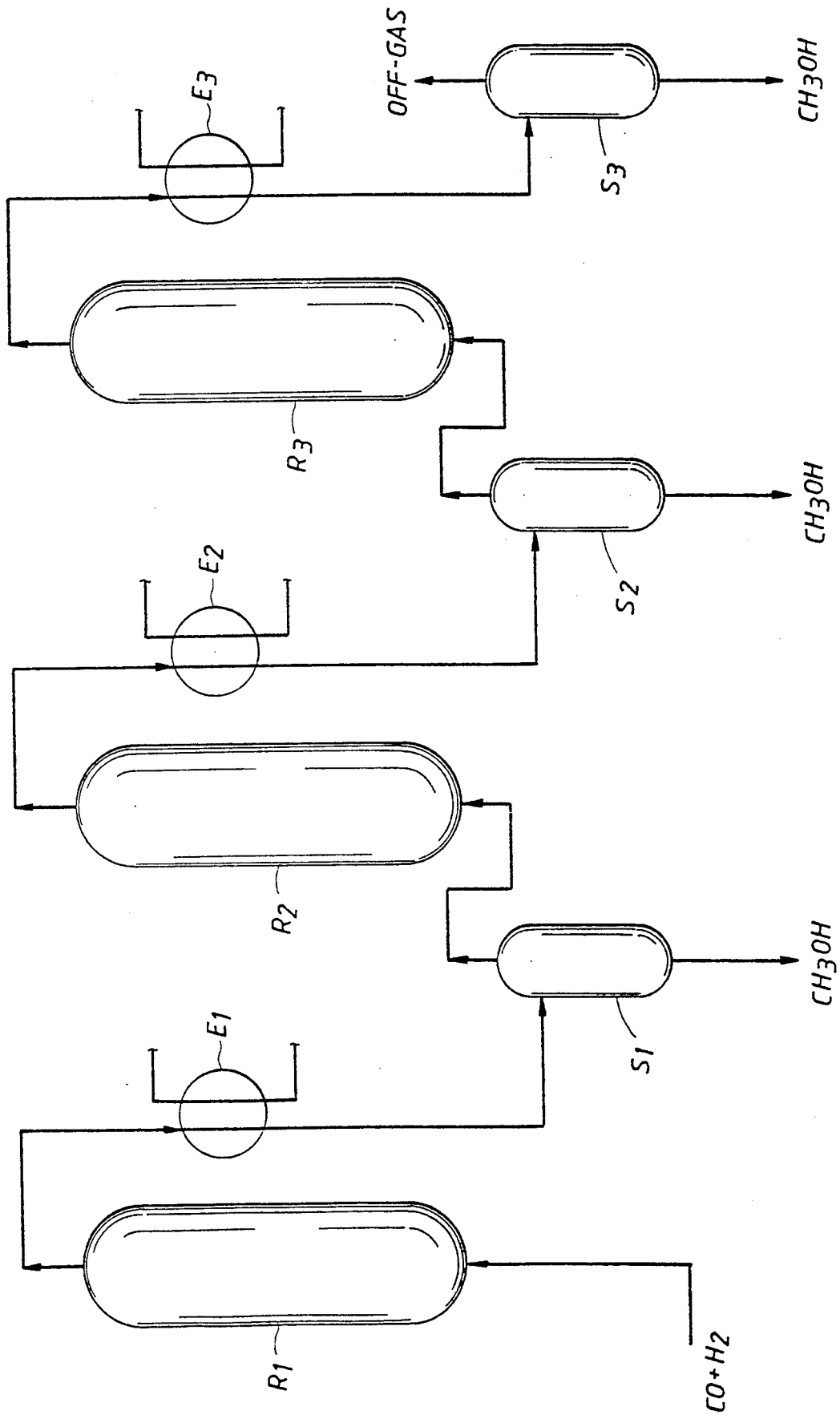

PROCESS FOR THE PRODUCTION OF METHANOL

FIELD OF THE INVENTION

The invention relates to a process for the production of methanol by reacting a gaseous mixture comprising hydrogen and carbon monoxide in the presence of a catalyst composition in a fluidized bed while cooling.

BACKGROUND OF THE INVENTION

Processes for the production of methanol by reacting a gaseous mixture comprising hydrogen and carbon monoxide in the presence of a catalyst composition in a fluidized bed have been disclosed in the prior art. Also it is known in the art to use a slurry of a heterogeneous catalyst in an inert liquid for this reaction.

A lecture reporting work by Y. Saito, M. Kuwa and O. Hashimoto during the 1987 Annual Meeting of the American Institute of Chemical Engineers, New York, Nov. 15–20, 1978, entitled "Development of a fluidized-bed methanol synthesis process" discloses a process using a reactor with the catalyst in a fluidized bed, cooled by means of a cooling jacket covering the surrounding wall of the bed. The temperature was adjusted by the temperature of the coolant (water being converted into high pressure steam). This process requires high space velocities and causes a considerable drop in pressure over the reactor, the conversion per pass was about 16%. Unconverted carbon monoxide and hydrogen were recompressed and recycled through the reactor.

A lecture reporting work by M. F. M. Post; S. T. Sie and J. M. Oelderik during the Chemeca '88 (Australia's Bicentennial International Conference for the process industries), Sydney Aug. 28–31, 1988, entitled "Synthesis of Methanol in A Fluidized Bed of Catalyst" discloses fluidized bed methanol synthesis at bench scale with conversions up to 60% at 8.1 MPa and 250° C. (523° K.) and good catalyst stability. For commercial operations the conversions were too low however.

Also there is Chemical Week, 36 Apr. 16, 1980) disclosing a process known as Chem Systems' three-phase process in which an inert liquid was used to fluidize the catalyst and to remove the heat of reaction. Good conversions per pass are claimed, however, the inert liquid caused transport problems and affected the reaction rate. The process also required separation of methanol from the entrained inert liquid.

Cheap methanol in very large quantities is valuable product as a fuel and a starting material for further chemical processing. Therefore there is a need for an economically attractive industrial bulk manufacturing process, using cheap starting materials and operating under attractive economical, environmental and safe conditions, i.e. using rather simple equipment and resulting in a significant reduction of the methanol cost price. Therefore, considerable research and development efforts have been made for a further improved methanol manufacturing process.

The formation of methanol from hydrogen and carbon monoxide is a strongly exothermic equilibrium reaction so that relatively high operating pressures and temperatures are required for reasonable reaction rates, but under such reaction conditions the attainable conversion is strongly limited by the thermodynamic equilibrium. Finding a satisfactory compromise as to the reaction conditions between reaction rate and conversion percentage is therefore difficult. Effective control of the reaction temperature across the catalyst bed proved to be especially important.

In industrially applied processes, in which the catalyst is present in the form of a fixed bed of particles, high gas velocities are applied to promote effective removal of reaction heat and to allow good control of the reaction temperature. Due to these high velocities and the thermodynamic limitations low conversions per pass (i.e. less than 30%) are obtained. To achieve acceptable yields of methanol from synthesis gas it is customary to recompress unconverted synthesis gas and recycle it to the reactor inlet. This requires recycle compressors of large capacities, which are costly and have high power consumptions.

An object of the present invention is the development of an industrial process for methanol manufacture with satisfactory conversion percentages in relatively simple equipment.

SUMMARY OF THE INVENTION

The present invention provides a process for the production of methanol by reacting a gaseous mixture comprising hydrogen and carbon monoxide in the presence of a catalyst in a plurality of fluidized catalyst bed reactors in series with interstage removal of methanol from the reaction mixture.

BRIEF DESCRIPTION OF THE DRAWING

The sole drawing is a flowsheet of an installation comprising three reactors in series which is suitable for carrying out the process of the present invention.

DETAILED DESCRIPTION OF THE INVENTION

The gaseous mixture fed into the reactors comprises hydrogen and carbon monoxide in a molar ratio $H_2:CO = 1$ to $3:1$, preferably between 1.5 to 2.5:1, more preferably around 2:1. Synthesis gas obtained by partial oxidation of methane with oxygen ($H_2:CO = 2:1$), is a recommended starting material, synthesis gas obtained by reforming of methane and/or carbon dioxide ($H_2:CO = 3:1$) can also be used.

The reaction temperature depends on the activity of the catalyst composition employed. In the case of an active catalyst the temperature may be as low as 100° C., but may be as high as 350° C.

The pressure in the reaction zone is usually in the range of from 5 to 35 MPa and again this is dependent on the activity of the catalyst composition employed and with active catalysts pressures below 10 MPa can be used. According to the present process conditions are chosen so as to achieve per pass conversions of at least 50%.

The catalyst compositions employed in the practice of this invention may suitably comprise e.g. copper/zinc optionally promoted with another element such as aluminum or chromium, on a carrier such as e.g. carbon, silica and/or alumina. Catalyst materials comprising copper and zinc optionally promoted with another element are preferred. Particle size and distribution of the catalyst material must be suitable for fluidized bed or made so e.g. by grinding and sieving. A particle size below 0.4 millimeter is generally suitable. Also adequate resistance of the catalyst towards attrition is important.

Interstage removal of methanol can e.g. be effected by cooling and condensation or by adsorption/absorption to a solvent. Cooling and condensation are preferred and are conveniently effected in a heat exchanger connected to a gas/liquid separator. The gaseous phase from which methanol has been removed can then be directly fed into the next reactor (without reheating or recompressing).

On a practical scale it is recommended to use a series of reactors with interstage removal of methanol in which each next reactor has a smaller capacity than the previous one, alternatively it is feasible to use e.g. groups of parallel reactors in series wherein the number of parallel reactors in each next group (and consequently their total capacity) is smaller than in the previous group and where interstage removal of methanol is effected between the groups of reactors.

More in particular it is preferred to use a plurality of reactors in series of which at least one (but preferably all of them) comprises a plurality of interconnected fluidized bed sections whereby each section is cooled by at least one heat exchanger and whereby the temperature in the highest section is reduced to below the (highest) temperature in a lower section. More preferably the highest section of the catalyst bed is cooled by at least one heat exchanger cooled with a mixture containing hydrogen and carbon monoxide such as cold feed gas. The temperature in at least one lower section of the catalyst bed can be controlled by adjusting the temperature of a heat exchanger converting water into high pressure steam. Preferably the heat exchangers of the feedgas/reaction mixture flow in countercurrent with each other. The various sections of the fluidized catalyst bed can be in one reactor, or each fluidized catalyst bed section can be present in a separate reactor of a series of interconnected reactors. The terms "highest" and "lower" refer obviously to the one reactor embodiment, but have a corresponding meaning with respect to the incoming gas feed and effluent when more than one reactor are employed.

Usually the highest temperature in the lower section(s) of the fluidized catalyst bed is between 200° C. and 350° C., often between 250° C. and 320° C., and it is preferred to employ reactors wherein the temperature in the highest section of the fluidized catalyst bed is 10 to 100 centigrades, preferably at least 25 centigrades, lower than the highest temperature in a lower section of the catalyst bed. Any fluidized bed sections in between the lowest and highest section should preferably be cooled to a temperature above the temperature of the highest section.

According to a preferred embodiment of the invention high pressure steam generated in the lowest section of the fluidized catalyst bed is used for purposes outside the present process, whereas the coolant gas of the highest section is the incoming gas feed which is preheated, preferably by means of a feed gas pre-heater located in the reactor.

This embodiment of the invention has the advantage of high conversions in relatively simple equipment, also it offers the possibility of a high throughput. Further advantages which can be achieved by this embodiment are that the temperature of the highest section of the fluidized bed and consequently the temperature of the effluent of the reactor can be lower than the mean temperature of the reactor which results in a higher temperature and consequently a higher reaction rate in the lower section(s) of the fluidized bed and a higher conversion percentage in the upper section and consequently also of the effluent.

An advantage that can be secured according to a preferred embodiment of the present invention is that the temperature and quality of the high pressure steam generated in the lower section(s) of the catalyst bed is increased.

A further advantage of the process according to the present invention is that it is possible to replenish the catalyst while the reaction is operated, catalyst stability requirements can be sacrificed in favor of higher activity so that it is possible to carry out the reaction at an unusually high temperature in the lower (main) section(s) of the catalyst bed providing additional room to improve space-time-yield. Consequently there is additional room to increase the temperature (quality) of the high pressure steam generated.

The invention is further elucidated by the attached drawing (FIG. 1), which represents a flowsheet of an installation suitable for carrying out the process of the invention and comprises a number of reactors ($R_1$, $R_2$, $R_3$) in series with a catalyst in a fluidized bed, which reactors are equipped with at least one heat exchanger, an inlet for synthesis gas and an outlet for reaction mixture, which outlet is connected to a heat exchanger ($E_1$, $E_2$, or $E_3$), which in turn is connected to a gas/liquid (methanol) separator ($S_1$, $S_2$, or $S_3$), having an outlet for unconverted synthesis gas, which in turn is connected to a next fluidized bed reactor and so on.

By selecting suitable reaction conditions and an active catalyst, such as $H_2:CO=67:32$, $T=250°-200°$ C., $P=8$ MPa and a reduced $Cu$—$ZnO$—$Cr_2O_3$-catalyst having a particle size below 0.1 millimeter, it is possible to obtain a degree of conversion of more than 60% per pass through the reactor, this is followed by interstage removal of methanol formed, preferably by cooling and condensation and the remaining gaseous phase is then passed through another reactor, which reactor could be smaller than the first reactor, the procedure of interstage removal of methanol formed and using the gaseous phase as the feed gas for another reactor is repeated a number of times. After multiple stages an overall yield of at least 90% of the feed gas of the first reactor can thus be obtained and methanol formed separated by interstage removal between the reactors. A methanol purity of over 98% can be obtained.

It is clear that in case the incoming feed gas of the first reactor is e.g. synthesis gas containing more than 2 moles of hydrogen per mole of carbon monoxide that after three or more passes through a reactor and interstage removal of methanol a hydrogen rich effluent gas is obtained. By applying membrane separation to this hydrogen rich gas it is possible to obtain chemically pure hydrogen.

EXAMPLE

Synthesis gas having the molecular composition of 67% $H_2$, 32% CO and 1% $CO_2$ is converted to methanol in three reactors in series, each containing a fluidized bed of catalyst in which cooling tubes are present to remove the reaction heat. Boiler feed water passing through the tubes is partly converted to saturated steam of high pressure and the mixture of water and steam is separated in a steam drum. The steam produced is used as process steam, whereas the water is recycled to the inlet of the cooling tubes. The pressure of the steam generation circuit is set according to the desired temperature in the fluidized bed.

Each of the reactors is filled with a fluidizable catalyst containing copper, zinc and chromium in the atomic ratio of 25/48/27 in the form of microspheres of an average diameter of 50 microns. The catalyst is prepared according to the procedure disclosed in U.S. Pat. No. 4,522,938, issued Jun. 11, 1985, which is herein incorporated by reference, for catalyst 5 described therein. The amounts of catalysts in the first, second and third reactor correspond to the weight ratio of 100:45:20 respectively. Before use, the catalyst in each reactor is activated by reduction in a flow of hydrogen gas at a pressure of 100-500 kPa and 220° C.

The synthesis gas used as feed is preheated to 230° C. and fed to the bottom of the first reactor. The space velocity in the first reactor amounts to 3500 Nm$^3$ per m$^3$ of settled catalyst per hour. The inlet pressure of the first reactor is 8 MPa, and the average bed temperature amounts to 250° C. The reactor effluent from the top of the reactor having a molar composition of 45.1% H$_2$, 21.3% CO, 0.8% CO$_2$ and 32.8% CH$_3$OH is cooled to about 30° C. and led to a gas-liquid separator where the major part of the methanol formed is separated off as liquid methanol. The gaseous stream leaving the separator having the molar composition 66.4% H$_2$, 31.4% CO, 1.2% CO$_2$ and 1% CH$_3$OH, is heated to about 230° C. and fed to the bottom of the second reactor. This reactor is operated at an inlet pressure of 7.5 MPa, an average temperature of 250° C. and a space velocity of 3200 Nm$^3$ per m$^3$ of settled catalyst per hour.

The reactor effluent from the top of the second reactor having a molar composition of 44.6% H$_2$, 20.7% CO, 1.0% CO$_2$ and 33.7% CH$_3$OH, is cooled to about 30° C. and led to a second gas-liquid separator where the major part of the methanol is separated off as liquid methanol. The gaseous stream from the second separator having a molecular composition of 66.5% H$_2$, 30.8% CO, 1.5% CO$_2$ and 1.2% CH$_3$OH, is heated to about 230° C. and fed to the bottom of the third reactor. This reactor is operated at an inlet pressure of 7 MPa, an average temperature of 250° C. and a space velocity of 2900 Nm$^3$ per m$^3$ settled catalyst per hour. The reactor effluent withdrawn from the top of the third reactor having a molar composition of 49.9% H$_2$, 22.2% CO, 1.3% CO$_2$ and 26.5% CH$_3$OH, is cooled to about 30° C. and led to a third gas-liquid separator where the major part of methanol is withdrawn as liquid methanol.

The conversion of CO in the first, second and third reactor amounts to 60, 60 and 58%, respectively. The total conversion of CO amounts to 93%. The amounts of methanol withdrawn from the first, second and third separator are 19.3, 8.1 and 2.4 moles per 100 moles of original synthesis gas feed. The total amount of methanol is 29.8 moles per 100 moles of synthesis gas, which represents 90.3% of the theoretical yield.

The ranges and limitations provided in the instant specification and claims are those which are believed to particularly point out and distinctly claim the instant invention. It is, however, understood that other ranges and limitation that perform substantially the same function in substantially the same manner to obtain the same or substantially the same result are intended to be within the scope of the instant invention as defined by the instant specification and claims.

What is claimed is:

1. A process for the production of methanol by reacting a gaseous mixture comprising carbon monoxide and hydrogen in a molar ratio H$_2$:CO = 1 to 3:1 hydrogen and carbon monoxide in the presence of a catalyst composition comprising copper and zinc in a fluidized bed while cooling, wherein:
   a. the reaction is carried out in a plurality of fluidized catalyst bed reactors in series with interstage removal of methanol from the reaction mixture by cooling and condensation or by absorption/absorption to a solvent;
   b. at least one of said fluidized bed(s) in said fluidized catalyst bed reactors from (a) is divided in a plurality of interconnected fluidized bed sections arranged in sequence in the direction of flow of the gaseous mixture whereby each section is cooled by at least one heat exchanger and whereby the temperature in the last section in sequence is reduced from 10 to 100 centigrades below the highest temperature in the preceding section(s);
   c. the conversion per pass through the reactors is at least 50 %; and
   d. the operating conditions of the reactors are within the temperature range from 200° to 350° C. and the pressure is within the range from 5 to 35 Mpa.

2. The process according to claim 1, wherein the molar ratio of carbon monoxide and hydrogen in the gaseous mixture is in a molar ratio H$_2$:CO = 1.5 to 2.5:1.

3. The process according to claim 1, wherein the last section in sequence of the catalyst bed is cooled by at least one heat exchanger cooled with a gas mixture comprising hydrogen and carbon monoxide.

4. The process according to claim 3, wherein effluent from said heat exchanger comprising said gas mixture comprising hydrogen and carbon monoxide is used as feed gas for said process.

5. The process according to claim 1, wherein the temperature in a least one section other than the last section in sequence of the catalyst bed is controlled by adjusting the temperature of a heat exchanger converting water into steam.

6. A process for the production of methanol by reacting a feed gas mixture comprising carbon monoxide and hydrogen in a molar ratio H$_2$:CO = 1 to 3:1 hydrogen and carbon monoxide in the presence of a catalyst composition comprising copper and zinc optionally promoted with an element selected from the group consisting of aluminum and chromium in a fluidized bed reactor while cooling, wherein:
   a. the reaction is carried out in a plurality of fluidized catalyst bed reactors in series with interstage removal of methanol from the reaction mixture or by adsorption/absorption to a solvent;
   b. at least one of said fluidized bed(s) in said fluidized catalyst bed reactors from (a) is divided in a plurality of interconnected fluidized bed sections arranged vertically in sequence in the direction of flow of the gaseous mixture;
   c. each section of said fluidized bed from (b) is cooled by at least one heat exchanger, wherein the lowest section of the fluidized bed is cooled by a heat exchanger which converts water into high pressure steam, and said feed gas mixture comprising carbon monoxide and hydrogen is first introduced as coolant to a heat exchanger designed to cool the highest section of the fluidized bed, whereby the temperature in the highest section is reduced from 10 to 100 centigrades to below the highest temperature in a lower section and whereby the said feed gas mixture is warmed to a higher temperature;
   d. the effluent which comprises said warmed feed gas mixture exiting from the heat exchanger of the highest section of the fluidized bed from (c) is passed to the lowest section of the fluidized bed to be used as feed gas for making methanol;

e. the conversion per pass through the reactors is at least 50%; and
f. the operating conditions of the reactors are within the temperature range from 200° to 350° C. and the pressure is within the range from 5 to 35 Mpa.

* * * * *